United States Patent [19]

Hill

[11] 4,057,630

[45] Nov. 8, 1977

[54] ANTIARTHRITIC COMPOSITIONS COMPRISING BIS-COORDINATED GOLD(1+) SALTS AND METHODS OF PRODUCING ANTIARTHRITIC ACTIVITY

[75] Inventor: David Taylor Hill, North Wales, Pa.

[73] Assignee: SmithKline Corporation, Philadelphia, Pa.

[21] Appl. No.: 710,506

[22] Filed: Aug. 2, 1976

[51] Int. Cl.$^2$ .............................................. A61K 31/66
[52] U.S. Cl. ..................................... 424/204; 424/198
[58] Field of Search ................................ 424/204, 198

[56] References Cited

U.S. PATENT DOCUMENTS

| | | | |
|---|---|---|---|
| 3,676,554 | 7/1972 | McGusty et al. | 424/198 |
| 3,718,680 | 2/1973 | McGusty et al. | 424/198 |

OTHER PUBLICATIONS

Aust. J. Chem. 19, 547 (1966).

Primary Examiner—Stanley J. Friedman
Attorney, Agent, or Firm—Joseph A. Marlino; Richard D. Foggio; William H. Edgerton

[57] ABSTRACT

Pharmaceutical compositions having antiarthritic activity comprising phosphine or phosphite bis-coordinated gold(1+) salts and methods of producing antiarthritic activity by administering internally, preferably orally, said compositions.

14 Claims, No Drawings

ANTIARTHRITIC COMPOSITIONS COMPRISING BIS-COORDINATED GOLD(1+) SALTS AND METHODS OF PRODUCING ANTIARTHRITIC ACTIVITY

This invention relates to novel pharmaceutical compositions having antiarthritic activity and to methods of producing antiarthritic activity by administering said compositions. More specifically, the compositions of this invention comprise phosphine or phosphite bis-coordinated gold(1+) salts as the active medicament.

The novel pharmaceutical compositions of this invention, in dosage unit form, comprise a nontoxic pharmaceutical carrier and a phospine or phosphite bis-coordinated gold(1+) salt represented by the following structural formula:

$$[(R_3P)(R_3'P)]Au^\oplus X^\ominus$$

Formula 1 wherein:

R and R' which may be the same or different represent phenyl, lower alkyl or lower alkoxy of from 1 to 4 carbon atoms, and X represents halide, perchlorate or tetrafluoroborate.

Mono phosphine or phosphite coordination complexes of gold(1 ) halides are known to have antiarthritic activity. This disclosure is set forth in U.S. Pat. No. 3,676,554. However, the bis-coordinated complex salts of this invention show not only improved antiarthritic properties but a surprisingly different biological profile and differ in structure and physical properties from these prior art compounds. Unlike the prior art mono-coordinated complexes, solutions of the compounds of this invention in polar solvents such as ethanol are good conductors of electricity indicating considerable dissociation. The prior art compounds also exhibit a greater preference for non-polar solvents and have only slight water solubility while the bis-coordinated gold(1+) salts are readily water soluble as reflected in their partition coefficient. For example, the partition coefficient (octanol/water) of the prior art chlorotriethylphosphinegold determined by the U. V. Hansch method is 17.2. The coefficient of the bis(triethylphosphine)gold(1+) chloride, a compound of this invention is 0.095.

Compounds of this invention also show more favorable oral absorptive properties than the prior art compounds.

At equivalent oral doses the serum gold levels produced by a preferred compound of this invention, bis(-triethylphosphine)gold(1+) bromide is approximately 45% higher than the prior art gold compounds. This is also accompanied by greater antiarthritic activity. For example, the above noted compound of this invention is 25% more active than the prior art compounds when measuring their ability to inhibit adjuvant-induced polyarthritis in rats.

The compounds of this invention also unexpectedly differ qualitatively in biological profile. Subnormal levels of serum sulfhydryl groups and elevated macroglobulins have been observed in various connective tissue diseases including patients suffering from rheumatoid arthritis (Evaluation of the Activity of Rheumatoid Arthritis, Haataja, M.:Scandinavian J. Rheumatology Vol. 4, Suppl. No. 7, 1975). Many drugs which are beneficial in the treatment of rheumatoid arthritis such as gold sodium thiomalate and nonsteroidal antiinflammatory agents alter sulfhydryl group reactivity as measured by a sulfhydryl-disulfide interchange reaction between rat serum sulfhydryl groups and dithiobisnitrobenzoic acid (Walz, D., DiMartino, M. J., Proc. Soc. Exp. Biol. and Med., 140,263–268(1972)).

Whereas prior art gold compounds such as gold sodium thiomalate and chlorotriethylphosphinegold are potent inhibitors of this interchange reaction, the above noted preferred compound of this invention markedly accelerates this reaction both in vitro and in vivo. This acceleration could be due either to serum protein interaction or dithiobisnitrobenzoic acid reaction with the preferred compound present in the serum.

This qualitative difference in disulfide interaction is biologically evident in that the compounds of this invention reduce the hemagglutination titers of 19S antibody (macroglobulins) in rat serum whereas the prior art gold compounds have no effect at comparable concentrations.

The compounds of Formula 1 are either known or are prepared by methods known in the literature. For example, the appropriately substituted phosphine or phosphite in a non-reactive organic solvent is mixed with the corresponding halophosphinegold compound. The solution is evaporated to dryness and recrystallized to give the desired bis phosphines or phosphites. Reference may be made to Aust. J. Chem. 19, 547, 1966.

The antiarthritic activity of the compositions of this invention is measured by the ability of the active medicament to inhibit adjuvant-induced polyarthritis in rats. The active medicaments of Formula 1 produce marked inhibition of the development of adjuvant arthritis in rats at daily oral doses as low as 10 mg. (calculated on gold content) per kilogram of body weight. Adjuvant arthritis in rats is produced by a single injection of 0.75 mg. of *Mycobacterium butyricum* suspended in white paraffin (N.F.) into a hindpaw (left footpad). The injected paw becomes inflamed and reaches a maximum volume in three to five days (primary lesion). The animals exhibit a decrease in body weight gain during this initial period. Adjuvant arthritis (secondary phase) occurs after a delay of approximately ten days and is characterized by inflammation of the non-injected sites (right hind leg), decrease in body weight gain and further increases in the volume of the injected hind leg. The compounds of Formula 1 administered in the dose described above beginning on the day of adjuvant injection and continuing for 17 days thereafter, exclusive of days 4, 5, 11 and 12, protect the animals against development of both primary and secondary lesions of adjuvant arthritis.

The pharmaceutical compositions of this invention are prepared in conventional dosage unit forms by incorporating an amount of a compound of Formula 1 sufficient to produce antiarthritic activity, without toxic effects, with a nontoxic pharmaceutical carrier according to accepted procedures. Preferably the compositions will contain as phosphine or phosphite gold Formula 1 in an amount of from about 0.5 mg. to about 5 mg., calculated on gold content, per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like.

Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

The pharmaceutical dosage unit forms described hereinabove exclude simple non-sterile solutions of the active medicament in water or in common organic solvents and exclude simple aqueous suspensions of the active medicament in the absence of a suspending agent.

The method in accordance with this invention comprises administering internally to an animal organisms a phosphine or phosphite bis-coordinated gold(1+) compound of Formula 1, usually combined with a pharmaceutical carrier, in an amount sufficient to produce antiarthritic activity without toxic effects. The active medicament will be administered in a dosage unit, preferably in an amount of from about 0.5 mg. to about 5 mg., calculated on gold content. The route of administration may be orally or parenterally, the oral route being preferred. Advantageously equal doses will be administered one or two times daily with the daily dosage regimen being from about 0.5 to about 10 mg., calculated on gold content. When the method described above is carried out antiarthritic activity is produced with a minimum of side effects.

The pharmaceutical preprarations are made following the conventional techniques of the pharmaceutical chemist involving mixing, granulating and compressing when necessary, or variously mixing and dissolving the ingredients as appropriate to the desired end product.

The following examples illustrate the preparation of compounds of Formula 1 and their incorporation into pharmaceutical compositions of this invention and as such are not to be construed as limiting the invention as set forth in the claims appended hereto.

EXAMPLE 1

A solution of 0.89 g. of trimethylphosphine in 100 ml. of ether was stirred under nitrogen and a solution of 3.63 g. of chloro(trimethylphosphine)gold in 50 ml. of methylene chloride was added. The mixture was stirred for 30 minutes at room temperature and the solvent evaporated to dryness in vacuo. The solid residue was recrystallized from chloroformether to give bis(trimethylphosphine)gold(1+) chloride as white crystals having a melting point of 182°-186° C.

EXAMPLE 2

In like manner using the procedure of Example 1, triethylphosphine and chloro(triethylphosphine)gold were employed as the starting materials to yield bis(triethylphosphine)gold(1+) chloride as a white solid having a melting point of 123°-125° C.

EXAMPLE 3

To a solution of 4.9 g. of chloro(trimethylphosphite)gold in 200 ml. of methanol was added 1.72 g. of trimethylphosphite followed by the addition of 2.68 g. of silver tetrafluoroborate in 70 ml. of methanol. The mixture was filered and the volume of the filtrate reduced to 40 ml. in vacuo. The filtrate was cooled to $-15°$ C. resulting in the white crystalline bis(trimethylphosphite)gold(1+) tetrafluoroborate having a melting point of 103°-106° C.

EXAMPLE 4

A solution of 4.68 g. of bis(triethylphosphine)gold(1+) chloride in 50 ml. of acetone was added to a solution of 2.07 g. of silver perchlorate in 200 ml. of acetone. The mixture was stirred at room temperature for two hours, filtered and the solvent was removed at reduced pressure. The resultant solid was recrystallized from methylene chloride to yield bis(triethylphosphine)gold(1+) perchlorate as white crystals having a melting point of 83°-86° C.

EXAMPLE 5

A solution of 3.0 g. of bis(triethylphosphine)gold(1+) chloride in 50 ml. of acetone was added to a solution of 0.64 g. of sodium tetrafluoroborate in 100 ml. of acetone. The mixture was stirred two hours at room temperature and the solvent removed in vacuo. The resultant solid was extracted with chloroform and the extracts were dried, filtered and the solvent removed in vacuo. The crude product was recrystallized from acetone-ether to give 2.0 g. of bis(triethylphosphine)gold(1+) tetrafluoroborate having a melting point of 125°-129° C.

EXAMPLE 6

To a solution of 2.5 g. of chloro(triisopropylphosphine)gold and 0.8 g. of sodium tetrafluoroborate in 120 ml. of acetone was added 1.2 g. of triisopropylphosphine in 25 ml. of acetone. The mixture was stirred four hours at room temperature and the solvent removed in vacuo. The resultant solid was dissolved in a minimum of hot acetone, filtered and cooled to give 2.0 g. of bis(triisopropylphosphine)gold(1+) tetrafluoroborate having a melting point of 206°-211° C.

EXAMPLE 7

| Ingredients | Mg./Tablet |
| --- | --- |
| Bis(triethylphosphine)gold(1+) bromide | 0.5 |
| Calcium sulfate, dihydrate | 150 |
| Sucrose | 25 |
| Starch | 15 |
| Talc | 5 |
| Stearic acid | 3 |

The sucrose, calcium sulfate and bis(triethylphosphine)gold(1+) bromide are thoroughly mixed and granulated with hot 10% gelatin solution. The wetted mass is passed through a No. 6 mesh screen directly onto drying trays. The granules are dried at 120° F. and passed through a No. 20 mesh screen, mixed with the starch, talc and stearic acid and compressed into tablets.

In like manner, the other bis phosphine or phosphite gold complexes disclosed herein may be formulated into tablets.

One tablet is taken twice a day.

EXAMPLE 8

| Ingredients | Mg./Capsule |
| --- | --- |
| Bis(triethylphosphine)gold(1+) chloride | 5 |
| Magnesium stearate | 5 |

| Ingredients | Mg./Capsule |
|---|---|
| Lactose | 400 |

The above ingredients are screened through a No. 40 mesh screen, mixed and filled into No. 0 hard gelatin capsules.

Similarly, the other phosphine or phosphite biscoordinated salts of this invention may be formulated into capsules.

One capsule is taken once a day.

EXAMPLE 9

A solution of 14 g. of thiodiglycol in 35 ml. of ethanol was added to a solution of 22.1 g. of gold acid chloride trihydrate in 105 ml. of distilled water at 0° C. A solution of 10 g. of phenyldiethylphosphine in 35 ml. of ethanol was then added dropwise. After stirring for 30 minutes the mixture was extracted with chloroform and the chloroform extracts dried, filtered and the solvent removed in vacuo to give an oil. Purification of this oil by "drycolumn" chromatography and recrystallization from ether gave chlorodiethylphenylphosphinegold as white crystalline material having a melting point of 61°–63° C.

A solution of 0.84 g. of diethylphenylphosphine in 20 ml. of acetone was added to 2.0 g. of chlorodiethylphenylphosphinegold and 0.6 g. of sodium tetrafluoroborate in 80 ml. of acetone at room temperature. After two hours the mixture was filtered and the solvent removed in vacuo. The solid residue was washed with ether and dissolved in acetone. Ether was added to the cloud point and then cooled to give bis(diethylphenylphosphine)gold(1+) tetrafluoroborate as white crystals having a melting point of 87°–89° C.

EXAMPLE 10

A solution of 1.0 g. of chlorotriphenylphosphinegold in 15 ml. of methylene chloride was added to 0.3 ml. of triethylphosphine in 30 ml. ether at room temperature. After stirring for one hour the solvents were removed in vacuo and the residue recrystallized from benzene-hexane to give crystalline (triethylphosphine)(triphenylphosphine)gold(1+) chloride, having a melting point of 98° C. (dec.).

What is claimed is:

1. A pharmaceutical composition hvaing antiarthritic activity, in dosage unit form, comprising a pharmaceutical carrier and an effective, nontoxic amount of a phosphine or phosphite bis-coordinated gold(1+) salt of the formula:

$$[(R_3P)(R_3'P)]Au^+X^-$$

in which:
R and R' which may be the same or different are phenyl, lower alkyl or lower alkoxy; and
X is halide, perchlorate, or tetrafluoroborate.

2. A pharmaceutical composition according to claim 1 in which both R and R' are lower alkyl.

3. A pharmaceutical composition according to claim 2 in which X is halide.

4. A pharmaceutical composition according to claim 3 in which both R and R' are ethyl and X is chloride.

5. A pharmaceutical composition according to claim 3 in which R and R' are ethyl and X is bromide.

6. A pharmaceutical composition according to claim 1 in which R is lower alkyl and R' is phenyl.

7. A pharmaceutical composition according to claim 6 in which R is ethyl and R' is phenyl.

8. The method of producing antiarthritic activity which comprises administering internally to an animal organism in an amount to produce said activity a phosphine or phosphite bis-coordinated gold(1+) salt of the formula:

$$[(R_3P)(R_3'P)]Au^+X^-$$

in which:
R and R' which may be the same or different are phenyl, lower alkyl or lower alkoxy; and
X is halide, perchlorate, or tetrafluoroborate.

9. The method according to claim 8 in which both R and R' are lower alkyl.

10. The method according to claim 9 in which X is halide.

11. The method accoring to claim 10 in which R and R' are ethyl and X is chloride.

12. The method according to claim 10 in which R and R' are ethyl and X is bromide.

13. The method according to claim 8 in which R is lower alkyl and R' is phenyl.

14. The method according to claim 13 in which R is ethyl and R' is phenyl.